US006140285A

United States Patent [19]

Banks et al.

[11] Patent Number: 6,140,285

[45] Date of Patent: Oct. 31, 2000

[54] USE OF DIOCTYL SULFOSUCCINATE SALTS FOR CLEANING PETROLEUM CONTAMINATED SURFACES

[75] Inventors: David M. Banks; Michael J. Bosse; Martha H. Meyer; Ralph A. Meyer, Jr.; Laura S. Phieffer; Kevin L. Smith, all of Charlotte, N.C.

[73] Assignee: Charlotte-Mecklenburg Hospital Authority, Charlotte, N.C.

[21] Appl. No.: 09/524,484

[22] Filed: Mar. 13, 2000

Related U.S. Application Data

[63] Continuation of application No. 09/126,353, Jul. 30, 1998, abandoned.

[51] Int. Cl.[7] .............................. C11D 17/00; A61K 7/50

[52] U.S. Cl. .......................... 510/130; 510/132; 510/159; 510/426; 510/505

[58] Field of Search .................................... 510/130, 132, 510/159, 426, 505

[56] References Cited

U.S. PATENT DOCUMENTS

| | | | |
|---|---|---|---|
| 3,924,004 | 12/1975 | Chang et al. | 424/358 |
| 4,111,844 | 9/1978 | Polony et al. | 252/106 |
| 4,434,090 | 2/1984 | Ampson et al. | 252/547 |
| 4,508,634 | 4/1985 | Elepano et al. | 252/163 |
| 4,879,062 | 11/1989 | Moore | 252/315.1 |
| 4,885,310 | 12/1989 | Kern | 514/547 |
| 4,975,217 | 12/1990 | Brown-Skrobot et al. | 252/107 |
| 5,045,366 | 9/1991 | Sedun | 427/440 |
| 5,169,622 | 12/1992 | Kopolow et al. . | |
| 5,186,857 | 2/1993 | Ramirez et al. | 252/167 |
| 5,219,890 | 6/1993 | Boucher | 514/705 |
| 5,280,042 | 1/1994 | Lopes | 514/557 |
| 5,357,636 | 10/1994 | Dresdner, Jr. et al. | 2/161 |
| 5,387,375 | 2/1995 | Erilli et al. | 252/546 |
| 5,490,992 | 2/1996 | Andrews et al. | 424/606 |
| 5,618,468 | 4/1997 | Canevari et al. | 252/354 |

FOREIGN PATENT DOCUMENTS

| | | | |
|---|---|---|---|
| 2 216 888 | 1/1998 | Canada | C09K 3/18 |
| 0 672 747 A2 | 9/1995 | European Pat. Off. | C11D 3/83 |
| 1 524 448 | 9/1978 | United Kingdom | C11D 7/50 |

OTHER PUBLICATIONS

W. Thompson, B. Herschman, P. Unthank, D. Pieper, and D.Hawtof, Toxicity of cleaning Agents for removal of grease from wounds; Ann–Plast–Surg.; 24(1):40–4; Jan. 1990.

R.J. Stratta, J.R. Saffle, M. Kravitz, and G.D. Warden, Management of tar and asphalt injuries; Am–J–Surg.; 146(6);766–9; Dec. 1983.

P.E. Luner, Wettability of a hydrophobic drub by surfactant solutions, Int. J. Pharm. 128(1–2):29–44, 1996.

D.W. Osborne, Micromulsions as Topical Drug Delivery Vehicles: In–Vitro Transdermal Studies of a Model Hydrophilic Drug, J Pharm Pharmacol 43(6):451–454, 1991.

M. Pedersen, Synergistic Action of Clotrimazole and Certain Anionic Surfactants May ge Due to Ion Pair Formation, Acta Pharm Nord 2(6):367–370, 1990.

J.R. Hart, M.T. DeGeorge, Lathering Potentials of surfactants—a simplified approach to measurement, J Soc Cosmet Chem 31(3):223–236, 1980.

G. Rodenheaver, V. Turnbull, and M.T. Edgerton, Pharmacokinetics of a new skin wound cleanser, Am J. Surg 132:67–74, 1976.

G. T. Rodeheaver, S.I. Smith, J.G. Thacker, M.T. Edgerton, and R.F. Edlich, Mechanical cleansing of conaminated wounds with a surfactant, Am J. Surg 129(3):241–245, 1975.

McIntyre Group, Ltd., *A Guide to Formulating Mild Sulfosuccinate Products.*

Galaxy Surfactants, Ltd., Fatty Alcohol Sulfates; Fatty Alcohol Ethoxy Sulfates; Sulfosuccinates; Foam and Viscosity Boosters; and Pearlising Agents, Internet site pages: www.galaxysurfactants.com,1997.

Unicure, Moisturizing Body Wash, Internet site pages: www.unicure.com/products/bodywash.htm, 1998.

National Starch & Chemical, 8822:113 Aerosol Hair Spray, Internet site pages: www.55voc.com/8822–113.htm, 1998.

*Primary Examiner*—Necholus Ogden
*Attorney, Agent, or Firm*—Alston & Bird LLP

[57] ABSTRACT

A composition for cleaning petroleum contaminated surfaces includes 5 to 60 percent by weight of a dioctyl sulfosuccinate salt, 20 to 50 percent by weight of a carrier composition and 10 to 75 percent by weight of a diluent. The preferred carrier composition is a mixture of polyethylene glycol and glycerol. The preferred diluent is water. The preferred concentration of sodium dioctyl sulfosuccinate is about 7% by weight. The preferred dioctyl sulfosuccinate salt is sodium dioctyl sulfosuccinate. A method of cleaning petroleum contaminated surfaces is also provided. The steps include providing a solution containing dioctyl sulfosuccinate salt, a carrier composition, and a diluent as described above and treating the petroleum contaminated surface with the solution in a manner and for a time sufficient to decontaminate the surface. The preferred method of treatment comprises contacting the solution with the petroleum contaminated surface for a time sufficient to create an emulsion and then removing the emulsion. The composition can be used to clean tissue.

8 Claims, No Drawings

USE OF DIOCTYL SULFOSUCCINATE SALTS FOR CLEANING PETROLEUM CONTAMINATED SURFACES

CROSS-REFERENCE TO RELATED APPLICATIONS

This application is a continuation of U.S. application Ser. No. 09/126,353, filed Jul. 30, 1998, now abandoned.

FIELD OF THE INVENTION

The present invention relates to cleaning compositions and methods of applying such compositions, and more particularly relates to compositions and methods of application suitable for treating petroleum contaminated surfaces.

BACKGROUND OF THE INVENTION

To ensure proper healing and prevent infection, a wound and the surrounding tissue must be cleaned thoroughly. Many industrial injuries, particularly machine related injuries, are difficult to treat due to the presence of petroleum based compounds at or near the site of the wound. Petroleum based compounds are particularly difficult to remove from the area of the wound because of a lack of effective cleansing agents.

Current accepted practices for treating petroleum contaminated tissue include surgical scrub preparation followed by thorough irrigation and debridement of grossly contaminated tissue. Extensive soft tissue debridement is often required in cases where the extent of petroleum contamination is severe.

Naturally, the irrigation and debridement process can be extremely painful to the patient. Additionally, such procedures cause considerable irritation to the sensitive tissue around the area of the wound. Undesirably, the treatment itself becomes a source of trauma to the patient. Thus, there is a need in the art for a method of cleaning petroleum contaminated tissue without necessitating excessive debridement and the accompanying tissue irritation. A cleaning composition that is suitable for use on a variety of surfaces is also desirable.

SUMMARY OF THE INVENTION

The present invention provides a method and composition for treating petroleum contaminated surfaces using a dioctyl sulfosuccinate salt as the cleaning agent. A solution containing a dioctyl sulfosuccinate salt may be applied to the contaminated surface for removal of petroleum based compounds. The present invention is suitable for removal of petroleum-based compounds from various surfaces, including tissue. Where the treated surface is tissue, use of the composition of the present invention greatly reduces the extent of debridement necessary to clean the tissue.

The present invention provides a composition for cleaning petroleum contaminated surfaces comprising 5 to 60 percent by weight of a dioctyl sulfosuccinate salt, 20–50 percent by weight of a carrier composition and 10–75 percent by weight of a diluent. Preferably, the dioctyl sulfosuccinate salt concentration is about 5 to about 15 percent by weight. Most preferably, the concentration of dioctyl sulfosuccinate salt is about 7 percent by weight. In one embodiment, the contaminated surface is tissue.

A suitable carrier composition comprises one or more alcohols. Most preferably the carrier composition is either glycerol, polyethylene glycol or mixtures thereof. In a preferred embodiment, the carrier composition comprises about 10 to 25 percent by weight of polyethylene glycol and about 10 to 25 percent by weight of glycerol. Other suitable carrier solvents include propylene glycol, polysorbate, mineral oil, hydroxypropyl methylcellulose, glycerol monooleate and stearyl alcohol. A preferred diluent is water.

A method of cleansing surfaces contaminated with a petroleum compound is also provided. The method involves providing a solution comprising the components described above and treating the contaminated surface with the solution in a manner and for a time sufficient to decontaminate the surface. Preferably, the contaminated surface is treated by contacting the contaminated surface with the solution for a time sufficient for the solution to form an emulsion with the petroleum compound or compounds. The resulting emulsion is then removed using any conventional technique, such as rinsing or irrigating the surface or wiping the affected surface with a sponge or cloth.

DETAILED DESCRIPTION OF THE INVENTION

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art.

The present invention provides a composition for cleaning petroleum contaminated surfaces. The composition includes a dioctyl sulfosuccinate salt dissolved in a solvent or carrier composition. The balance of the composition comprises a diluent.

The composition of the present invention is suitable for cleaning a variety of petroleum contaminated surfaces. The composition can be used to clean petroleum contaminated tissue, clothing, household objects, industrial machinery or other surfaces. As used herein, the term "tissue" is intended to refer to all exposed surfaces on a human or animal body, including skin and hair, to which a topical solution may be applied. The tissue to be cleaned may be either intact or broken, such as the site of a wound. The present composition is useful for cleaning tissue in an emergency care or preoperative procedure during the treatment of industrial, military or household accidents involving petroleum contamination. In an environmental disaster involving a petroleum spill, the composition of the present invention could aid the treatment of wildlife contaminated with petroleum compounds. Further, the present invention is useful for general household or industrial use to clean surfaces contaminated with petroleum-based compounds.

Dioctyl sulfosuccinate can be found in sodium, potassium or calcium salt form. A preferred dioctyl sulfosuccinate salt is sodium dioctyl sulfosuccinate. Sodium dioctyl sulfosuccinate is available as a wax-like solid that is sparingly soluble in water and freely soluble in alcohol. Sodium dioctyl sulfosuccinate has known surface-active properties and is a commonly used ingredient in laxatives and cerumenolytics. Further, sodium dioctyl sulfosuccinate is used as an anionic surfactant in microbicidal and anti-fungal compositions.

In the present invention, a dioctyl sulfosuccinate salt in solution is used to remove petroleum based compounds from contaminated surfaces. Where the surface is tissue, the cleaning solution of the present invention cleans the contaminated tissue without excessive debridement and irritation. It is believed that the dioctyl sulfosuccinate salt forms an emulsion with the petroleum based compounds that greatly increases the ease of removal. Preferably, the composition contains 5 to 60 percent by weight of a dioctyl sulfosuccinate salt. More preferably, the composition contains 5 to 15 percent by weight of a dioctyl sulfosuccinate salt. Most preferably, the concentration of dioctyl sulfosuccinate salt is about 7 percent by weight.

The upper concentration limit for the dioctyl sulfosuccinate salt is based on an increase in toxicity at higher concentrations. Use of the cleaning solution of the present invention on tissue would not be recommended at concentrations above the upper limit disclosed herein. However, in cases where toxicity is not a major concern, higher concentrations of dioctyl sulfosuccinate salt may be used.

The dioctyl sulfosuccinate salt is dissolved in a solvent or carrier composition in order to efficiently deliver the dioctyl sulfosuccinate salt to the contaminated tissue in solution form. The carrier composition may be any suitable solvent known in the art. For compositions that are intended for use on tissue, a carrier composition should be chosen that causes minimal irritation to sensitive tissue.

A suitable carrier composition comprises one or more alcohols. Most preferably, the carrier composition is polyethylene glycol, glycerol or mixtures thereof. Other possible solvents include propylene glycol, polysorbate, mineral oil, hydroxypropyl methylcellulose, glycerol monooleate and stearyl alcohol. A preferred concentration of the carrier composition is 20 to 50 percent by weight. A preferred carrier composition comprises about 10 to 25 percent by weight of polyethylene glycol and about 10 to 25 percent by weight of glycerol.

A diluent is added to the dioctyl sulfosuccinate salt solution to reach the desired final concentration of the dioctyl sulfosuccinate salt. Any diluent known in the art may be used. As with the carrier composition, the diluent must cause minimal tissue irritation for compositions designed for use on tissue. A preferred diluent is water. Preferably, the diluent concentration is between 10 to 75 percent by weight. Most preferably, the diluent concentration is about 20 to 75 percent by weight. In one preferred embodiment, the diluent concentration is about 40 to 75 percent by weight.

A method of cleansing a petroleum contaminated surface is also provided by the present invention. The method includes providing a solution containing a dioctyl sulfosuccinate salt, a carrier composition, and a diluent as described above. The solution is then used to treat the petroleum contaminated surface, such as tissue, in a manner and for a time sufficient to decontaminate the surface. The preferred method of treatment is to bring the solution containing dioctyl sulfosuccinate salt into direct contact with the petroleum contaminated surface. The dioctyl sulfosuccinate salt solution is believed to form an emulsion with the petroleum compounds. Once the emulsion is formed, the petroleum contamination and solution may be removed by any conventional method. For example, removal may be accomplished by irrigating or rinsing the affected surface or by wiping the surface with a cloth or sponge.

EXAMPLE

A cleaning solution was prepared in the following manner. 50 grams of sodium dioctyl sulfosuccinate available from Sigma was mixed with 100 ml of polyethylene glycol and 100 ml of glycerol. The resulting mixture was agitated for 15 minutes. 400 ml of water was added to the mixture to dilute the concentration of sodium dioctyl sulfosuccinate to about 7 percent by weight. The mixture was agitated thoroughly.

Sixty previously euthanized Sprague Dawley rats were randomized to one of twelve cohort groups. Each animal was subjected to a contamination protocol followed by a cleansing procedure. Petroleum contaminants included: commercially available refined motor oil, multipurpose axle grease, roofing tar, and crude oil obtained from Mobil Oil corporation. Cleansing agents included: commercially available dioctyl sulfosuccinate sodium syrup (Colace, 20 mg/5 ml of docusate sodium, 0.4%), standard surgical scrub solution (Hibiclens), and our solution of 7% pure sodium dioctyl sulfosuccinate in polyethylene glycol and glycerol solvent prepared as described above. The dorsum of the animals were shaved and an initial 8 mm circular punch biopsy (Sample A) was obtained. The animals were then contaminated with one of the four contaminants and allowed to stay for thirty minutes. After excess contaminant was removed, a pre-cleansing 8 mm punch biopsy (Sample B) was obtained. Each animal then underwent a standardized two minute scrub and rinse protocol with one of the three scrub solutions after which a post-cleansing 8 mm punch biopsy (Sample C) was obtained. The three samples obtained from each animal were then analyzed, in a blinded fashion, using standard fluorometry techniques with an Aminco Bowman Series 2 Luminescent Spectrometer. Assays were based on the natural fluorescence of polyaromatic hydrocarbons in petroleum products. Quantification of contaminant reduction following scrubbing with the respective cleansing solution was then calculated.

Standard statistical methods were employed. Means and SEM were calculated. Significant differences were evaluated by one way analysis of variance with the LSD multiple comparisons test. Data were tested for heterogeneity of variance and log transformations were done when appropriate. A p-value of less than 0.05 was considered significant. The 7% pure dioctyl sulfosuccinate solution showed significantly better performance in removing multipurpose axle grease ($p=0.02$), roofing tar ($p=0.001$), and crude oil ($p=0.02$) over the other cleansing agents tested.

Many modifications and other embodiments of the invention will come to mind to one skilled in the art to which this invention pertains having the benefit of the teachings presented in the foregoing descriptions. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A liquid composition for cleansing a petroleum contaminated surface, said composition consisting essentially of:

about 5 to about 15 percent by weight of a diocyl sulfosuccinate salt;

about 20 to about 50 percent by weight of a carrier composition, said carrier composition comprising glycerol and polyethylene glycol; and about 40 to about 75 percent by weight of water.

2. A liquid composition according to claim 1, wherein said carrier composition comprises:

about 10 to about 25 percent by weight of polyethylene glycol; and about 10 to about 25 percent by weight of glycerol.

3. A liquid composition according to claim 1, wherein said dioctyl sulfosuccinate salt comprises sodium dioctyl sulfosuccinate.

4. A liquid composition according to claim 1, comprising about 7 percent by weight of said dioctyl sulfosuccinate salt.

5. A liquid composition according to claim 1, wherein said carrier composition further comprises a component selected from the group consisting of propylene glycol, polysorbate, mineral oil, hydroxypropyl methylcellulose, glycerol monooleate, stearyl alcohol and mixtures thereof.

6. A liquid composition according to claim 1, wherein said petroleum contaminated surface comprises tissue.

7. A liquid composition for cleansing a petroleum contaminated surface, said composition consisting essentially of:

about 7 percent by weight of a dioctyl sulfosuccinate salt, about 10 to about 25 percent by weight of polyethylene glycol, about 10 to about 25 percent by weight of glycerol; and about 40 to about 75 percent by weight of water.

8. A liquid composition according to claim 7, wherein said dioctyl sulfosuccinate salt comprises sodium dioctyl sulfosuccinate.

* * * * *